United States Patent [19]

Karol

[11] Patent Number: 5,412,130

[45] Date of Patent: May 2, 1995

[54] METHOD FOR PREPARATION OF ORGANIC MOLYBDENUM COMPOUNDS

[75] Inventor: Thomas J. Karol, Norwalk, Conn.

[73] Assignee: R. T. Vanderbilt Company, Inc., Norwalk, Conn.

[21] Appl. No.: 255,690

[22] Filed: Jun. 8, 1994

[51] Int. Cl.⁶ .............................................. C07F 11/00
[52] U.S. Cl. ...................................... 556/57; 252/336; 252/42.7
[58] Field of Search .......................................... 556/57

[56] References Cited

U.S. PATENT DOCUMENTS

| | | | |
|---|---|---|---|
| 3,285,942 | 11/1966 | Westfield et al. | 260/429 |
| 4,164,473 | 8/1979 | Coupland et al. | 252/32.7 |
| 4,889,647 | 12/1989 | Rowan et al. | 252/42.7 |
| 5,137,647 | 8/1992 | Karol | 252/42.7 |

Primary Examiner—José G. Dees
Assistant Examiner—Porfirio Nazario-Gonzalez
Attorney, Agent, or Firm—Rasma B. Balodis

[57] ABSTRACT

A novel process for the preparation of 2,4-heteroatom substituted-molybdena-3,3-dioxacycloalkane compounds by reacting diol-, diamino-, thiol-alcohol and amino-alcohol compounds with a molybdenum source and in the presence of a phase transfer agent of the imidazoline type.

6 Claims, No Drawings

METHOD FOR PREPARATION OF ORGANIC MOLYBDENUM COMPOUNDS

BACKGROUND OF THE INVENTION

The present invention concerns a novel method for preparation of organic molybdenum compounds.

Generally, it is difficult to prepare organic molybdate compounds by known synthesis schemes. The prior art methods do not provide for effective incorporation of molybdenum into the reaction to afford the desired molybdate.

In the prior art, U.S. Pat. No. 5,137,647 teaches that fatty derivatives of 1-(2-hydroxyethyl)-2-imidazoline may be hydrolyzed to form an amine-amide intermediate which is reacted with a molybdenum source to form heterocyclic molybdenum complexes. U.S. Pat. No. 4,164,473 teaches that certain heterocyclic molybdenum compounds are prepared by reacting a tertiary amine having hydroxy or thiol groups and a molybdenum source. The reaction is carried out as a typical esterification reaction. The molybdenum compounds are useful as lubricating additives.

It has been now discovered that improved conversion to organic heterocyclic molybdates is obtained by using 2-hydroxyalkyl imidazoline compounds as molybdenum phase transfer agents to transfer molybdenum into certain organic receptor molecules under controlled conditions.

SUMMARY OF THE INVENTION

The present invention concerns a process for preparing heterocyclic molybdates by reacting diol-, diamino-, thiol-alcohol-and amino-alcohol-compounds with a molybdenum source and in the presence of a phase transfer agent to produce 2,4-heteroatom substituted-molybdena-3,3-dioxacycloalkane derivatives or mixtures thereof.

As used herein, the term diol-, diamino-, thiol - alcohol- and amino - alcohol - compounds refer to compounds derived from triglycerides, poly-alpha-olefins, polypropene, polybutylene, polyisobutylene, fatty acids, fatty oils, and fatty amides.

The term 2,4-heteroatom substituted-molybdena - 3,3-dioxacycloalkane - containing triglyceride - derived compounds is used herein to generically describe the heterocyclic compounds obtained by reacting the diol-, diamino-, thiol-alcohol - and amino - alcohol - triglyceride compounds in the presence of a molybdenum source and a phase transfer agent.

The term 2,4-heteroatom substituted - molybdena - 3,3 -dioxacycloalkane - fatty acid - derived compounds herein generically describes the heterocyclic compounds obtained by reacting the diol-, diamino-, thiol - alcohol and amino - alcohol - fatty acid compounds in the presence of a molybdenum source and a phase transfer agent.

The term 2,4 - heteroatom substituted - molybdena - 3,3-dioxacycloalkane - polymer- derived compounds herein generically describes the heterocyclic compounds obtained by reacting the diol -, diamino - , thiol - alcohol - and amino - alcohol - substituted poly-alpha-olefins, polypropene, polybutylene, or polyisobutylene in the presence of a molybdenum source and a phase transfer agent.

According to the invention, a process is disclosed for preparation of a 2,4 - heteroatom - substituted - molybdena - 3,3 -dioxocycloalkane composition by reacting a starting material having the structural formula

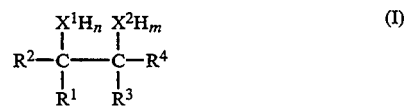

(I)

or

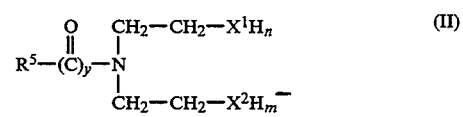

(II)

wherein $X^1$ and $X^2$ are selected from the group consisting of O, S or N and where n or m=1 when $X^1$ $X^2$ or is O or S and n or m=2 when $X^1$ or $X^2$ is N, y=0 or 1, and wherein $R^1$, $R^2$, $R^3$, $R^4$ and $R^5$ are independently selected from the group consisting of hydrogen, alkyl, alkenyl, aryl, alkylaryl hydrocarbon group or fatty residue containing from 1 to 50 carbon atoms or polymers having a molecular weight of 150 to 1200 and selected from poly-alpha-olefins, polypropene, polybutylene and polyisobutylene, with a molybdenum source in the presence of a phase transfer agent of formula

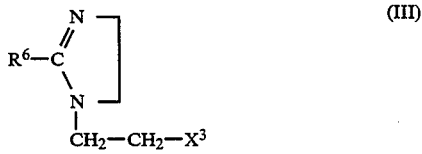

(III)

or

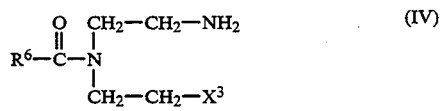

(IV)

wherein $X^3$ is a hydroxy or amino group and $R^6$ is an alkyl group or fatty acid residue having 8 to 22 carbon atoms, to yield 2,4-heteroatom - substitutued-molybdena - 3,3-dioxacyloalkane compound having the formula

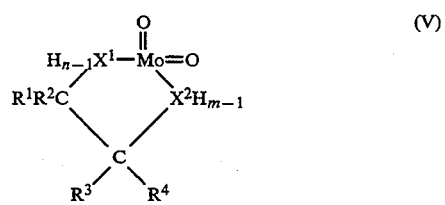

(V)

or

-continued

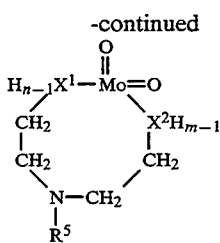

wherein $R^1$, $R^2$, $R^3$, $R^4$, $R^5$, $X^1$, $X^2$, n and m are as defined hereinabove and correspond to the starting materials of formula (I) and (II) respectively.

DETAILED DESCRIPTION OF THE INVENTION

Molybdates are difficult to prepare in high yields by prior art methods. Primarily, because it is difficult to incorporate molybdenum in the organic receptor molecule in sufficient quantities.

This improved process for preparation of molybdate compounds defined above utilizes a phase transfer agent for incorporating molybdenum into the receptor molecule. The phase transfer agent is of the formula (IV)

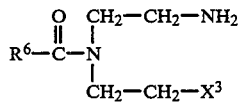

wherein $R^6$ is an alkyl group or a fatty acid residue having 8 to 22 carbon atoms and $X^3$ is a hydroxy or amino group.

Alternately, an imidazole compound of the formula (III) may be used as the phase transfer agent. Since the reaction is conducted in water media, the imidazole compound and will hydrolyze according to the following reaction scheme

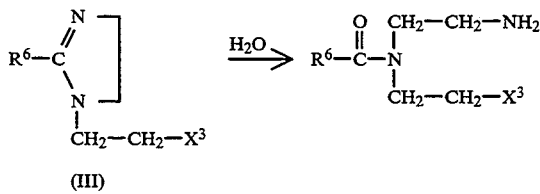

In the presence of water, the phase transfer agent forms a complex with molybdenum when one mole of the reaction water is removed, under controlled conditions, preferably at a temperature ranging from 60° to 150° C.

When the transfer complex is added to a receptor molecule having diol-, diamino-, thiol - alcohol - or amino - alcohol groups, molybdenum is transferred from the transfer complex to the receptor molecule to form a 2,4-heteroatom - substituted - molybdena - 3,3 - dioxacycloalkane compound of formula (V) or (VI) hereinabove. In the ring structure, the molybdenum atom is bound to the oxygen atom from an alcohol group and to either a second oxygen atom in the case of a diol, a sulfur atom in the case of a hydroxy-mercapto reagent or a nitrogen atom in the case of an amino-hydroxy reagent.

Alternately, an alkyl or a fatty derivative of 2-(2-aminoethyl)aminoethanol and a molybdenum source may be used to produce the molybdenum transfer complex.

The fatty residue may be derived from fatty oils or fatty acids. The fatty oils are glyceryl esters of higher fatty acids. Such esters are commonly known as vegetable and animal oils. Vegetable oils particularly useful are oils derived from coconut, corn, cottonseed, linseed, .peanut, soybean mid sunflower seed. Similarly, animal fatty oils such as tallow may be used. The fatty acids may be saturated or unsaturated. Particularly useful are lauric, palmitic, stearic, oleic, linoleic and linolenic acids. Preferred are fatty residues containing at least 8 carbon atoms and may contain 22 carbon atoms and higher. A particularly preferred transfer agent is 1-(2-hydroxyethyl)-2-octadecylimidazoline.

The source of molybdenum is an oxygen-containing molybdenum compound capable of reacting with the hydrolyzed imidazoline compound or a fatty derivative of 2-(2-aminoethyl)aminoethanol to form an ester type molybdenum complex. The sources of molybdenum include, among others, ammonium molybdates, molybdenum oxides and mixtures thereof. The molybdenum source is added in a sufficient quantity to yield about 2.0 to 20 percent, preferably 6.0 to 12.0 percent of molybdenum of the product.

The receptor molecules to which the molybdenum can be transferred by the process of the invention are organic compounds having diol, diamino - thiol - alcohol and amino alcohol functionality.

Suitable receptor compounds can be selected from polymers having 1,2-diol groups and molecular weight ranging from 150 to 1200 and higher. Preferred are epoxidized polyolefins, polypropene, polybutylene or polyisobutylene having 1,2-diol groups. Epoxidized polymers are available commercially. Suitable receptors are also the 1-hydroxy-2-thio analogs, 1- hydroxy -2 -amino analogs and 1,2 -diamino analogs of epoxidized polymers. The analogs are available commercially or they can be prepared by known methods. For example, the epoxidized polymer can be reacted with hydrogen sulfide in the presence a tertiary amine catalyst and water to yield the desired 1- hydroxy- 2 -thio—analog. The amino analogs may be prepared by reacting with aziridine.

Another receptor molecule includes vegetable and animal fatty oils having 1,2-diol groups or the analogous 1-hydroxy-2-amino-, 1-hydroxy-2-thio- or 1,2-diamino - groups. Preferred are fatty oils having 8 to 22 carbon atoms and higher. In particularly preferred are receptor molecules derived from tall oil such as 2-ethylhexyl-tallow oil and cocoamides such as cocodiethanolamide.

According to the invention, glyceride compounds can also serve as receptor molecules. Preferred are diol, thiol-alcohol and diamino derivatives of triglycerides. The fatty and triglyceride derivatives are available commercially. Alternately, the compounds may be prepared by hydroxylating an epoxidized triglyceride in the presence of an acid or base and then reacting with a suitable reagent to form 1,2-diol, 1,2-thiol-hydroxy and 1,2-amino-triglycerides in which the thiol, hydroxy and amino functional groups are attached to the adjacent carbon atoms originally contained in the epoxide ring structure. While peroxy acid and permanganate hydroxylation are known to yield stereochemically different products, either steriosomer can serve as a receptor molecule.

The transfer reaction is conducted at 70° to 150° C. and the reaction water as well as any diluent water is removed from the mixture by gas purge, distillation or vacuum distillation. The reaction may be conducted in an inert solvent.

The following examples are given for the purpose of further illustrating the invention. All percentages and parts are based on weight unless otherwise indicated.

EXAMPLE 1

A reactor was charged with triethylamine, 8 g, 2-pyrrolidone, 0.6 g, 2-beta-hydroxyethyloctadecylimidazoline, 0.6 g, water, 8 g, and molybdenum trioxide, 8 g. The reaction mixture was simultaneously stirred and refluxed for 30 minutes. 2-Hydroxyhexadecylthiol, 31.4 g, and diluent oil, 7.3 g, were added to the reaction. The flask was fitted with a Dean Stark trap filled with triethylamine and heated to 130°–135° C. to azeotrope diluent water and one mole reaction water from the reaction. The reaction was stripped of volatile solvents by applying vacuum and filtrated.

The product obtained was predominantly 1-tetradecyl-2-thio-3-molybdena-4-oxa-3,3-dioxocyclopentane having a molybdenum content of 7.6 percent. Additionally, the product is believed to contain a lesser amount of 1-tetradecyl-2-oxa-3-molybdena-4-thio-3,3-dioxocyclo-pentane.

EXAMPLE 2

A reactor was charged with concentrated ammonium hydroxide, 100 ml, dissolved in 200 ml isopropanol. Commercial epoxidized 2-ethylhexyl tallow-carboxylate, (Drapex manufactured by Witco Chemical Co.), 113 g was added with stirring and warmed to 80° C. for one hour. This intermediate alcohol-amine ester was isolated by diluting with acetone, 250 ml, filtering and rotary evaporating off the solvent.

The intermediate, 105.5 g, was converted to the molybdenum compound by charging with water, 24.6 g, ammonium heptamolybdate, 18.3 g, 2-beta-hydroxyethyloctadecylimidazoline, 6.3 g, 2-betahydroxyethyloctadecylimidazoline, 6.3 g and an antifoamant silicone oil-water emulsion, 0.25 ml. The reaction was stirred for one hour at 70°–80° C. Then it was heated to 135°–140° C. with simultaneous removal of solvent. Diluent water and one mole reaction water was collected and the product was isolated by filtration to afford a brownish green liquid with 7 percent molybdenum content.

EXAMPLE 3

A reactor was charged with epoxidized soybean oil, 300 g, water, 50 g, and 70% methanesulfonic acid, 1.3 g. The reaction was stirred and heated for three hours at 70°–75° C. Then the reaction was charged with water, 31 g, ammonium molybdate, 60 g, 2-betahydroxyethyloctadecylimidazoline, 21 g, and an antifoamant silicone oil-water emulsion, 0.25 ml and heated for one hour at 70°–75° C. The reaction was stripped of solvent with simultaneous heating to 135°–140° C., maintained at that temperature until no further water was produced and filtered. The product was a viscous green liquid with a molybdenum content of 3.38%.

EXAMPLE 4

A reactor was charged with epoxidized polyisobutylene, m. wt. 365, 300 g, water, 70 g, 70% methanesulfonic acid, 1.5 ml, and antifoamant silicone oil-water emulsion, 0.5 ml and heated to reflux for a period of ten hours. After cooling to 70°–80° C., the reaction was charged with concentrated ammonium hydroxide, 2 ml, ammonium heptamolybdate 60 g, and 2-beta-hydroxyethyloctadecylimidazoline 20 g. Water was azeotroped off by heating to 135°–140° C. The reaction was maintained under full vacuum for one hour and filtered hot to aford a green liquid product having about 9 percent molybdenum incorporation.

As illustrated by the examples, the molybdenum incorporated into the receptor molecules by the method of the invention is equimolar for simpler receptor molecules. For fatty derivatives and polymeric substances incorporation may be up to 20 percent and higher depending on the type of the receptor molecule.

The above embodiments have shown various aspects of the present invention. Other variations will be evident to those skilled in the art and such modifications are intended to be within the scope of the invention as defined by the appended claims.

What is claim is:

1. A process for preparing a 2,4-heteroatom-substituted molybdena-3,3-dioxocycloalkane compound comprising the steps of selecting a starting material having the structural formula

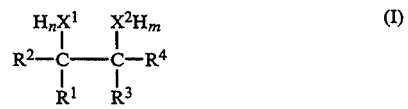

or

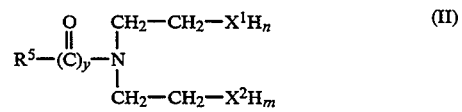

wherein $X^1$ and $X^2$ are selected from the group consisting of O, S or N and where n or m=1 when $X^1$ or $X^2$ is O or S and n or m=2 when $X^1$ or $X^2$ is N, y=0 or 1, and wherein $R^1$, $R^2$, $R^3$, $R^4$ and $R^5$ are independently selected from the group consisting of hydrogen, alkyl, alkenyl, aryl, alkylaryl hydrocarbon group or fatty residue containing from 1 to 50 carbon atoms or polymeric residues having a molecular weight of 150 to 1200; and selected from poly-alpha-olefin, polypropene, polybutylene and polyisobutylene; reacting the starting material with a molybdenum source sufficient to yield about 2 to 20 percent of molybdenum based on the weight of the molybdena-compound in the presence of water and a phase transfer agent of the formula

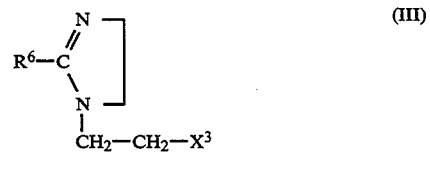

or

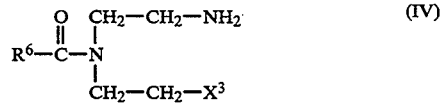

wherein $R^6$ is an alkyl group or fatty residue having 8 to 22 carbon atoms and $X^3$ is a hydroxy or amino group at 60° to 150° C.; removing the reaction water and diluent water and recovering the molybdena-compound of the formula

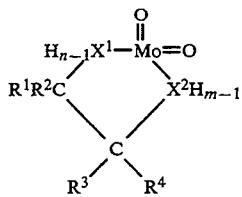 (V)

or

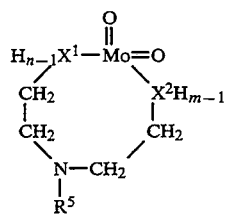 (VI)

wherein $R^1$, $R^2$, $R^3$, $R^4$, $R^5$, $X^1$, $X^2$, n and m are defined and correspond to the starting materials in formula (I) and (II).

2. A process for preparing a 2,4-heteroatom substituted molybdena-3,3-dioxocyclopentane compound according to claim 1 wherein the transfer agent is 1-(2-hydroxyethyl)-2-octadecylimidazoline.

3. A process for preparing a 2,4-heteroatom substituted molybdena-3,3-dioxocyclopentane compound according to claim 1 wherein the starting material of formula I is derived from epoxidized fatty oils or fatty acids.

4. A process for preparing a 2,4-heteroatom substituted molybdena-3,3-dioxocyclopentane compound according to claim 1 wherein the starting material of formula I is derived from triglycerides.

5. A process for preparing a 2,4-heteroatom substituted molybdena-3,3-dioxocyclopentane compound according to claim 1 wherein the starting material of formula I is derived from epoxidized polymers having a molecular weight in the range of 150 to 1200 and selected from poly-alpha-olefins, polypropene, polybutylene and polyisobutylene.

6. A process for preparing a 2,4-heteroatom substituted molybdena-3,3-dioxacycloalkane compound according to claim 1 wherein the molybdenum source is an aqueous solution of ammonium molybdate, or molybdenum trioxide.

* * * * *

UNITED STATES PATENT AND TRADEMARK OFFICE
CERTIFICATE OF CORRECTION

PATENT NO. : 5,412,130

DATED : May 2, 1995

INVENTOR(S) : Thomas J. Karol

It is certified that error appears in the above—identified patent and that said Letters Patent is hereby corrected as shown below:

At column 2, line 20

"$X^1X^2$ or is "should be --$X^1$ or $X^2$ is ---;

at column 3, line 39

"compound and will hydrolyze" should be

--compound will hydrolyze--;

at column 4, line 10

"soybean mid sunflower" should be

--soybean and sunflower--;

at column 6, line 21

UNITED STATES PATENT AND TRADEMARK OFFICE
CERTIFICATE OF CORRECTION

PATENT NO. : 5,412,130
DATED : May 2, 1995
INVENTOR(S) : Thomas J. Karol

It is certified that error appears in the above-indentified patent and that said Letters Patent is hereby corrected as shown below:

"What is claim is:" should be

--What is claimed is:--

Signed and Sealed this

Fourth Day of July, 1995

Attest:

BRUCE LEHMAN

Attesting Officer

Commissioner of Patents and Trademarks